US012539392B2

(12) United States Patent
Fitzgerald

(10) Patent No.: US 12,539,392 B2
(45) Date of Patent: Feb. 3, 2026

(54) INTRODUCER ASSEMBLY WITH SELECTABLE SIDE HOLES

(71) Applicant: Medtronic Vascular, Inc., Santa Rosa, CA (US)

(72) Inventor: Adam Fitzgerald, St. Louis Park, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 782 days.

(21) Appl. No.: 17/818,821

(22) Filed: Aug. 10, 2022

(65) Prior Publication Data

US 2023/0096007 A1 Mar. 30, 2023

Related U.S. Application Data

(60) Provisional application No. 63/247,919, filed on Sep. 24, 2021.

(51) Int. Cl.

| | |
|---|---|
| ***A61M 25/00*** | (2006.01) |
| ***A61M 39/02*** | (2006.01) |
| *A61M 25/06* | (2006.01) |

(52) U.S. Cl.

CPC ...... *A61M 25/007* (2013.01); *A61M 39/0247* (2013.01); *A61M 2025/0079* (2013.01); (Continued)

(58) Field of Classification Search

CPC ............ A61M 25/007; A61M 25/0662; A61M 29/00; A61M 39/0247; A61M 2025/0004; (Continued)

(56) References Cited

U.S. PATENT DOCUMENTS 4,968,306 A * 11/1990 Huss .................. A61M 25/007 604/275
4,995,865 A 2/1991 Gahara et al.
(Continued)

FOREIGN PATENT DOCUMENTS

EP 2133115 A1 12/2009

OTHER PUBLICATIONS

Medtronic, "Sentrant—Introducer Sheath with Hydrophilic Coating," Instructions for Use, M057826T001 Rev. 1A, 2017 (Applicant points out, in accordance with MPEP 609.04(a), that the year of publication, 2017, is sufficiently earlier than the effective U.S. filing date, so that the particular month of publication is not in issue.), 8 pp.

(Continued)

*Primary Examiner* — Benjamin J Klein
(74) *Attorney, Agent, or Firm* — Shumaker & Sieffert, P.A.

(57) ABSTRACT

An introducer assembly includes a plurality of selectable side holes through which a fluid can be delivered. In some examples, an introducer assembly includes an outer elongated body defining a plurality of outer body side holes and an inner elongated body defining a plurality of inner body side holes. The inner elongated body is configured to rotate relative to the outer elongated body between a first rotational orientation in which a first subset of outer body side holes aligns with a first subset of inner body side holes and the inner elongated body blocks fluid flow out of the outer elongated body through a second subset of outer body side holes, and a second rotational orientation in which the second subset of outer body side holes aligns with a second subset of inner body side holes and inner elongated body blocks fluid the first subset of outer body side holes.

19 Claims, 4 Drawing Sheets

(52) U.S. Cl.
CPC ............... *A61M 2025/0681* (2013.01); *A61M 2039/0258* (2013.01); *A61M 2039/0291* (2013.01)

(58) Field of Classification Search
CPC .. A61M 2025/0079; A61M 2025/0681; A61M 2025/0258; A61M 2025/0291
See application file for complete search history.

(56) References Cited

U.S. PATENT DOCUMENTS

| | | | | |
|---|---|---|---|---|
| 5,425,723 | A | 6/1995 | Wang | |
| 5,647,860 | A | 7/1997 | Roth et al. | |
| 6,488,662 | B2 | 12/2002 | Sirimanne | |
| 7,452,353 | B2 | 11/2008 | Dal Porto et al. | |
| 7,905,856 | B2 | 3/2011 | McGuckin, Jr. et al. | |
| 8,702,678 | B2 | 4/2014 | Comerota et al. | |
| 10,631,980 | B2 | 4/2020 | Costello | |
| 2005/0020976 | A1 | 1/2005 | Maki et al. | |
| 2005/0107738 | A1 | 5/2005 | Slater et al. | |
| 2006/0085029 | A1* | 4/2006 | Brightbill | A61B 17/00491 606/213 |
| 2007/0213671 | A1 | 9/2007 | Hiatt | |
| 2009/0170933 | A1 | 7/2009 | Leckrone | |
| 2011/0282195 | A1 | 11/2011 | Solar et al. | |
| 2012/0179144 | A1* | 7/2012 | Carleo | A61M 25/0017 604/544 |
| 2013/0274711 | A1* | 10/2013 | O'Day | A61M 39/08 604/508 |
| 2014/0257244 | A1 | 9/2014 | Johnston et al. | |
| 2014/0276656 | A1 | 9/2014 | Bian et al. | |
| 2015/0290421 | A1* | 10/2015 | Glickman | A61M 25/003 604/30 |
| 2016/0106954 | A1 | 4/2016 | Hebbard | |
| 2020/0360656 | A1 | 11/2020 | Sandquist et al. | |
| 2020/0376249 | A1* | 12/2020 | Lockhart | A61M 25/00 |
| 2021/0045723 | A1 | 2/2021 | Martin et al. | |

OTHER PUBLICATIONS

Extended Search Report from counterpart European Application No. 22196115.4 dated Mar. 2, 2023, 11 pp.

* cited by examiner

INTRODUCER ASSEMBLY WITH SELECTABLE SIDE HOLES

This application claims the benefit of U.S. Provisional Application No. 63/247,919, filed Sep. 24, 2021, and entitled, "INTRODUCER ASSEMBLY WITH SELECTABLE SIDE HOLES," the entire content of which is incorporated herein by reference.

TECHNICAL FIELD

The present disclosure relates to a medical introducer sheath.

BACKGROUND

An introducer sheath is configured to provide percutaneous access to vasculature of a patient and defines a lumen through which fluid (e.g., contrast agent or a therapeutic fluid) and/or one or more medical devices, such as catheters, can be introduced into the vasculature.

SUMMARY

In general, the present disclosure describes an introducer assembly configured to provide percutaneous access to vasculature of a patient and including selectable side holes through which fluid can be delivered into the vasculature. The disclosure also describes systems including the introducer assembly and methods of using the introducer assembly.

In examples described herein, an introducer assembly includes an inner elongated body and an outer elongated body defining a lumen configured to receive the inner elongated body. The outer elongated body defines a plurality of selectable outer body side holes and the inner elongated body defines a plurality of inner body side holes. When the inner elongated body is inserted in the lumen of the outer elongated body, one or more inner body side holes align with different subsets of outer body side holes (e.g., one or more outer body side holes and less than all the outer body side holes) depending on a relative rotational orientation of the outer and inner elongated bodies. When the one or more inner body side holes align are aligned with the subset of outer body side holes, fluid can flow from an inner lumen of the inner elongated body and through the subset of outer body side holes to exit the introducer assembly. In addition, the inner elongated body blocks fluid flow through the outer body side holes not aligned with an inner side hole. A clinician may therefore select a subset of outer body side holes through which fluid is to be delivered by at least changing the relative rotational orientation of the outer and inner elongated bodies.

By enabling a clinician to select a subset of outer body side holes of the outer elongated body, the clinician may better target fluid delivery at a desired location in the vasculature. For example, a vasodilating agent can be delivered through a subset of outer body side holes to target a specific location in a blood vessel to reduce vessel spasms at the specific location.

An introducer assembly including selectable side holes may also reduce the amount of fluid needed to achieve a desired result (e.g., reduce an amount of contrast agent needed to facilitate clinician visualization of the vasculature of the patient and/or reduce an amount of vasodilating agent needed to reduce vessel spasms). Reducing the amount of fluid needed to achieve the desired result may reduce patient discomfort, increase versatility, and reduce an amount of time needed to perform a particular medical procedure, as compared to introducer sheaths that only enable fluid delivery through a distal opening or simultaneously through all side holes.

In some examples, a medical assembly includes an outer elongated body defining an outer body lumen and a plurality of outer body side holes distributed longitudinally along the outer elongated body and open to the outer body lumen; and an inner elongated body defining an inner body lumen and a plurality of inner body side holes distributed longitudinally along the inner elongated body and open to the inner body lumen, the inner elongated body being configured to be inserted in the outer body lumen. When the inner elongated body is positioned in the outer body lumen, the inner elongated body is configured to rotate relative to the outer elongated body between: a first rotational orientation in which a first subset of outer body side holes aligns with a first subset of inner body side holes and in which the inner elongated body blocks a second subset of outer body side holes, and a second rotational orientation in which the second subset of outer body side holes aligns with a second subset of inner body side holes and in which the inner elongated body blocks the first subset of outer body side holes.

In some examples, an introducer assembly comprises an introducer sheath defining an introducer sheath lumen and a plurality of introducer sheath side holes distributed longitudinally along the introducer sheath and open to the introducer sheath lumen; and an inner member defining an inner member lumen and a plurality of inner member side holes distributed longitudinally along the inner member and open to the inner member lumen. When the inner member is inserted in the introducer sheath lumen, different subsets of introducer sheath side holes are configured to align with one more of the inner member side holes depending on a rotational orientation of the introducer sheath and the inner member to enable selective fluid delivery through a subset of introducer sheath side holes from the inner member lumen.

In some examples, a method comprises introducing a medical assembly described herein into vasculature of a patient, and rotating at least one of the inner elongated body or the outer elongated body of the medical assembly to position the inner elongated body in a first rotational orientation.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
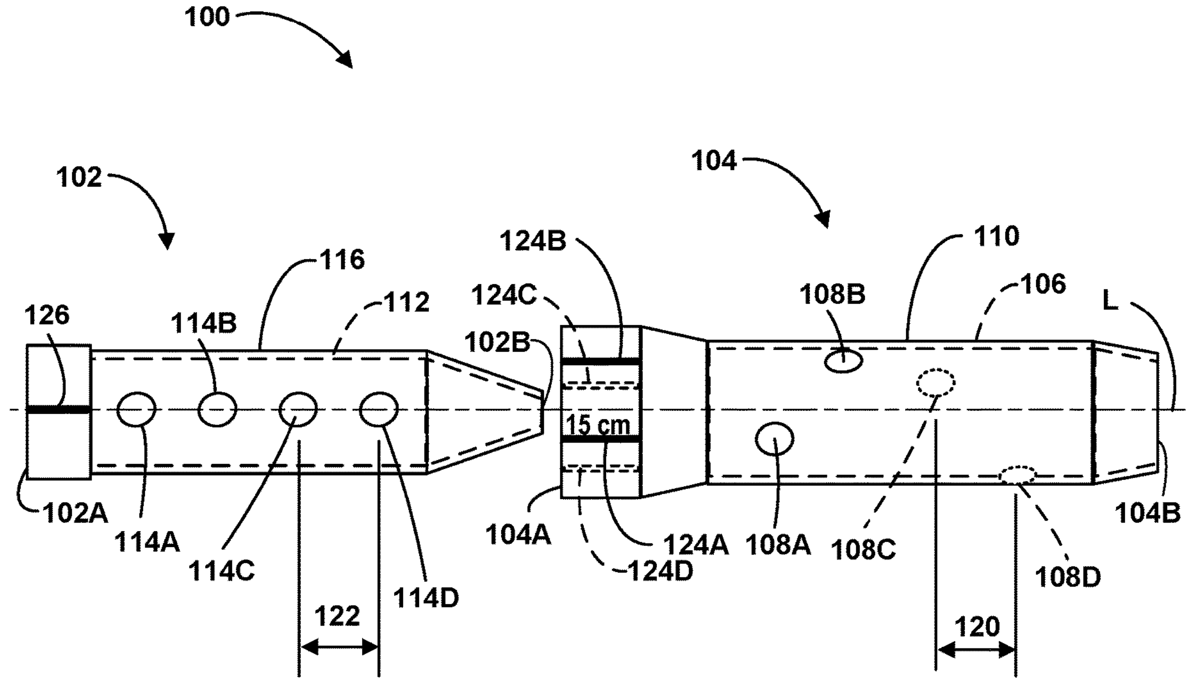
FIG. 1 is a conceptual diagram illustrating a side view of an example introducer sheath including an inner elongated body and an outer elongated body configured to receive the inner elongated body.

A medical assembly described herein includes selectable side holes through which fluid can be delivered into vasculature of a patient. The medical assembly is referred to herein as an introducer assembly, but may be used for other functions in other examples. The introducer assembly includes an outer elongated body (e.g., an introducer sheath) defining a first lumen configured to provide percutaneous access to vasculature of a patient and an inner elongated body (e.g., a dilator) configured to be received in the first lumen. The inner and outer elongated bodies each define a plurality of side holes, which are configured to align in different ways depending on the relative rotational orientation of the inner and outer elongated bodies. The introducer assembly defines a fluid flow pathway from a lumen of the inner elongated body and through aligned side holes, and the inner elongated body blocks fluid flow through the side holes of the outer elongated body that are not aligned with a side hole of the inner elongated body. A clinician may select a subset of side holes of the outer elongated body (referred to herein as "outer body side holes") through which fluid is to be delivered to vasculature of a patient by at least changing the relative rotational orientation of the outer and inner elongated bodies.

For example, in some examples, when in a first rotational orientation relative to the outer elongated body, the inner elongated body is configured to enable fluid flow out a first subset of outer body side holes of the outer member while blocking a second, different subset of outer body side holes to enable fluid flow out of outer elongated body through the first subset of outer side holes and block fluid flow out through the second subset of outer body side holes. When in a second rotational orientation relative to the outer elongated body, the inner elongated body is configured to block the first subset of outer body side holes while not blocking the second subset of outer body side holes to enable fluid flow out of outer elongated body through the second subset of side holes and block fluid flow out through the first subset of outer body side holes. Each subset of side holes described herein can include one or more side holes, and in examples, includes less than all the available side holes of the particular elongated body.

The introducer assemblies described herein may provide one or more advantages by enabling a clinician to selectively deliver fluid through outer body side holes at a desired axial position along a length of the outer elongated body. For example, an introducer assembly described herein can reduce an amount of fluid needed to achieve a desired result by enabling a clinician to better target fluid delivery at a desired location in the vasculature. Reducing an amount of fluid needed to be delivered to achieve a desired result may reduce patient discomfort, increase versatility, and reduce an amount of time needed to perform a particular medical procedure, as compared to introducer sheaths that only enable fluid delivery through a distal opening or simultaneously through all side holes. As another example, an introducer assembly including selectable side holes described herein may enable fluid to be delivered to vasculature with increased pressure, as compared to introducer sheaths that only enable fluid delivery simultaneously through all side holes.

Any suitable fluid can be delivered through the introducer assembly. In some examples, the fluid includes a contrast agent and with the aid of an introducer assembly including selectable side holes, a clinician can deliver the contrast agent to target a specific location in the vasculature, thereby reducing an amount of contrast agent needed to facilitate clinician visualization of the specific location in the vasculature.

As another example, a clinician can deliver a vasodilating agent through a selected subset of outer body side holes to target a specific location in a blood vessel to reduce vessel spasms at the specific location. When using an introducer sheath or the like to access vasculature of a patient during a medical procedure through an entry point (e.g., a femoral artery entry point, a radial artery entry point, or entry point into vasculature), vasospasms in the blood vessel may cause the vessel to collapse around the introducer sheath. The vessel walls may apply a constrictive force around the introducer sheath, which can make proximal retraction or distal advancement of the introducer sheath further into vasculature of a patient more difficult. Delivery of a vasodilating agent to the vasculature to prevent or reduce vasospasms may lessen the force on the introducer sheath and may improve maneuverability of the introducer assembly through the vasculature. Because the blood vessel may not spasm along the entire length of the introducer assembly, an introducer assembly including selectable side holes may help reduce the overall volume of vasodilating agent needed to reduce forces on the outer elongated body that may inhibit longitudinal advancement of the outer elongated body through the vasculature.

While introducer sheaths having only an open distal end or a plurality of non-selectable side holes may be useful for delivering a vasodilating agent, these introducer sheaths do not enable selective targeting of particular blood vessel locations. In some cases, however, only part of the blood vessel may be spasming, e.g., the part of the blood vessel near the entry point into the vasculature. Thus, delivery of a vasodilating agent into the vasculature of a patient from the distal end of an introducer sheath may not have a substantial effect on the vascular tissue that is spasming, e.g., the vascular tissue near the proximal portion of the introducer sheath. While a vasodilating agent may be dispersed from the distal end of an introducer device, tissue near the vasculature entry point may continue to exhibit vasospasm. Fluid dispersion from the distal end of the introducer device may thus require a higher volume of a vasodilating agent to effect tissue areas near the vasculature entry point.

The introducer assemblies described herein enable a more targeted delivery of vasodilating agent or another fluid to a particular location of a blood vessel compared to introducer sheaths having only an open distal end or a plurality of non-selectable side holes. For example, during a procedure in which an introducer device is inserted in vasculature of a patient, a clinician may decide to deliver a vasodilating agent to a particular region in the patient's vasculature. Without needing to retract or advance the introducer device relative to the entry point into the vasculature, the clinician may selectively deliver a vasodilating agent to a particular location along a length of the introducer assembly via manipulation of the introducer assembly to modify a relative rotational orientation of the inner and/or outer elongated bodies to select a particular subset of outer body side holes of the outer elongated body for fluid delivery.

The elongated bodies of the introducer assemblies described herein may be configured in a variety of different ways to enable selective fluid delivery at a plurality of locations along a length of the introducer assembly. In some examples, one of the outer elongated body or the inner elongated body defines a plurality of side holes distributed both circumferentially and axially (in a direction parallel to a longitudinal axis of the elongated body) along the respective elongated body, and the other of the outer elongated body or the inner elongated body defines a plurality of side holes distributed axially along the inner elongated body and axially aligned along the respective elongated body. When the inner elongated body is inserted in the lumen of the outer elongated body, the inner body side holes align with different one or more outer body side holes depending on a relative rotational orientation of the outer and inner elongated bodies. When inner body side holes are aligned with outer body side holes, fluid can flow from the lumen of the inner elongated body and through the outer body side holes to an environment external to the outer elongated body.

A clinician may select a subset of outer body side holes through which fluid is to be delivered by at least changing the relative rotational orientation of the outer and inner elongated bodies. For example, the inner elongated body can be configured to rotate relative to the first elongated body between at least a first rotational orientation and a second rotational orientation. In the first rotational orientation, a first subset of outer body side holes aligns with one or more inner side and in which the inner elongated body blocks a second subset of outer body side holes and in the second rotational orientation, the second subset of outer body side holes aligns with one or more inner body side holes and in which the inner elongated body blocks the first subset of outer body side holes.

In some examples, the inner and outer elongated bodies include visible markings that facilitate user selection of the outer body side holes through which fluid is to be delivered. The visible markings can, for example, indicate the longitudinal and/or circumferential position of one or more subsets of side holes of the respective elongated body.

The devices, assemblies (also referred to herein as systems), and methods described herein may be helpful for medical procedures in which vasculature of a patient is accessed through a radial artery, although other procedures may benefit from the advantages of the devices, systems, and methods described. In addition, the devices, assemblies, and methods described herein may also be well suited for injecting contrast in a contralateral access procedure at different lengths along the introducer device, such that both legs of a patient can be visualized under fluoroscopy without losing guidewire access across the iliac bifurcation.

FIG. 1 is a conceptual diagram illustrating a side view of an example introducer assembly 100, which is configured to facilitate percutaneous access to vasculature of patient for a medical procedure and includes selectable side holes through which fluid can be delivered to vasculature of a patient. Introducer assembly 100 includes an inner elongated body 102 and an outer elongated body 104 defining a lumen 106 configured to receive the inner elongated body 102. Lumen 106 of outer elongated body 104 can also be referred to as an outer body lumen, a first lumen, or an introducer sheath lumen in various examples described herein.

Figure 3:
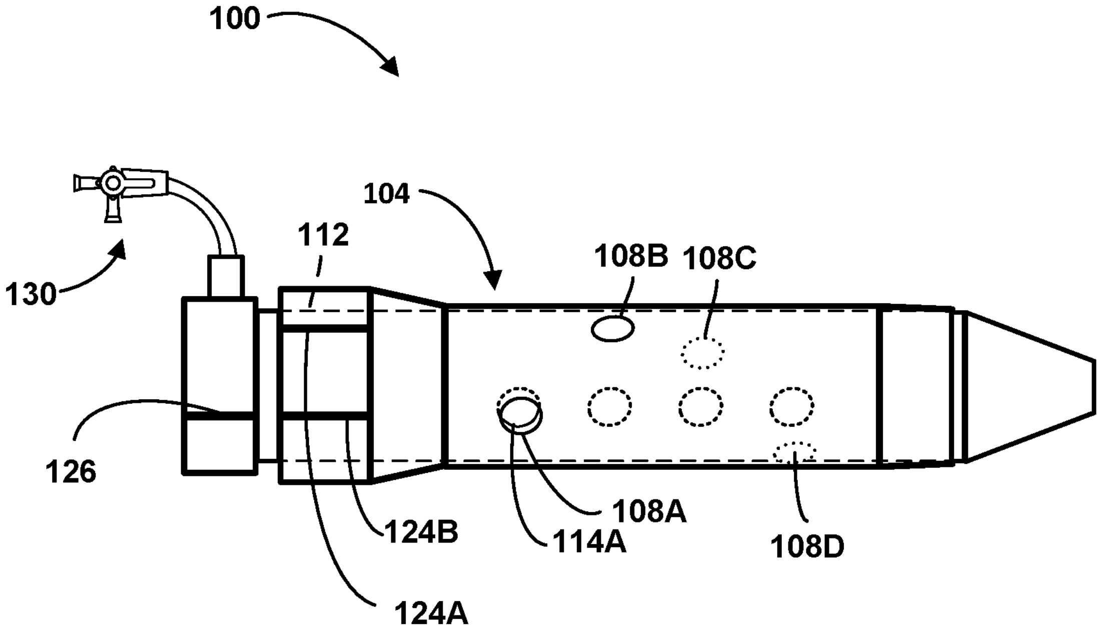
FIG. 3 is a conceptual diagram illustrating the introducer sheath of FIG. 1 and illustrates the inner elongated body is received in the outer elongated body.

FIG. 1 illustrates an unassembled view in which inner elongated body 102 is not yet inserted in outer body lumen 106. As discussed in further detail below, FIG. 3 illustrates an assembled view in which inner elongated body 102 is inserted in outer body lumen 106.

In some examples, outer elongated body 104 is more flexible than inner elongated body 102. For example, inner elongated body 102 can be or include a dilator or another suitable inner member, and outer elongated body 104 can be or include an introducer sheath or another suitable outer member. Inner and outer elongated bodies 102 can have any suitable relative lengths. In some examples, inner elongated body 102 is configured to extend distally past distal end 104B of outer elongated body 104. In other examples, inner elongated body 102 is configured such that distal end 102B remains within lumen 106 when inner elongated body 102 is fully inserted in outer elongated body 104.

Outer elongated body 104 defines a plurality of side holes 108A-108D (collectively referred to as side holes 108 or individually referred to as a side hole 108, and also referred to herein as outer body side holes or openings) that are open to outer body lumen 106 and define a passageway from outer body lumen 106 to outer surface 110 of elongated body 104. Thus, a fluid may flow from outer body lumen 106 to an environment external to outer elongated body 104 via outer body side holes 108. In some examples, outer body lumen 106 extends from a proximal opening at or near proximal end 104A of outer elongated body 104 to a distal opening at or near distal end 104B of outer elongated body 104. Thus, in some cases, fluid can flow through the distal opening as well as through outer body side holes 108. In some examples, outer body lumen 106 extends along an entire length of outer elongated body 104. In other examples, outer elongated body 104 has a closed distal end such that outer body lumen 106 terminates proximal to distal end 104B of elongated body 104.

Inner elongated body 102 defines a lumen 112 and a plurality of side holes 114A-114D (collectively referred to as side holes 114 or individually referred to as a side hole, and also referred to herein as inner body side holes or openings) open to lumen 112. Lumen 112 can also be referred to as an inner body lumen, a second lumen, or a dilator lumen in various examples described herein. In some examples, inner body lumen 112 extends from a proximal opening at or near proximal end 102A of inner elongated body 102 to a closed distal end 102B of inner elongated body 102. That is, distal end 102B of inner elongated body 102 may not define any openings, such that fluid through distal end 102B is blocked and such that inner body lumen 112 terminates proximal to distal end 102B of elongated body 102. In some examples, inner body lumen 112 only extends from the proximal opening at or near proximal end 102A to a distal-most inner side hole 114. Inner side hole 114 are open to inner body lumen 112 and define a passageway from inner body lumen 112 to an environment external to outer surface 116 of inner elongated body 102.

Fluid can be introduced into inner body lumen 112 using any suitable technique, such as by direct or indirect introduction, by introduction via a side port of a hub, handle, or the like at proximal end 102A of inner elongated body 102 or otherwise in fluid communication with proximal end 102A.

In some examples, outer body lumen 106 and/or inner body lumen 112 define a passageway through which a medical device (e.g., a guidewire, a catheter, an interventional device, such as a stent, a thrombectomy device, or the like), a fluid (e.g., a therapeutic agent, a vasodilating agent, or a contrast agent), or any combination thereof can be introduced into vasculature of a patient. Thus, outer body lumen 106 and/or inner body lumen 112 can be configured to receive the medical device, a fluid, or any combination thereof.

When inner elongated body 102 is inserted in outer body lumen 106, fluid can flow from inner body lumen 112 through side holes 108, 114 that are aligned, e.g., fully or partially overlap in a radial direction in examples in which elongated bodies 102, 104 have substantially circular cross sections (e.g., circular or nearly circular to the extent permitted by manufacturing tolerances). When so aligned, the side holes 108, 114 define a fluid pathway from inner body lumen 112 to an environment external to outer elongated body 104. That is, the one or more outer body side holes 108 that are aligned with respective one or more inner body side holes 114 are open and "unblocked" by inner elongated body 102, such that fluid can flow from inner body lumen 112, through one or more inner body side holes 114, and through the one or more outer body side holes 108 that are aligned with the one or more inner body side holes 114.

Inner body side holes 114 of inner elongated body 102 are distributed along inner elongated body 102 in a different way than outer body side holes 108 are distributed along outer elongated body 104. As a result, when inner elongated body 102 is inserted in outer body lumen 106 of outer elongated body 104, not all inner body side holes 114 align with outer body side holes 108. Instead, the alignment between one or more inner body side holes 114 and one or more outer body side holes 108 depends upon the relative rotational orientation between inner elongated body 102 and outer elongated body 104. A clinician can rotate elongated bodies 102, 104 relative to each other in order to align one or more inner body side holes 114 with different subsets of outer body side holes 108. The subset of outer body side holes 108 that is aligned with one or more inner body side holes 114 are the outer body side holes 108 that remain "unblocked" and that are open to inner body lumen 112 of inner elongated body 102. Thus, fluid can flow from inner body lumen 112 through aligned inner and outer body side holes 114, 108.

Elongated bodies 102, 104 having circular cross-sections (the cross-sections take in a direction orthogonal to longitudinal axis L) are primarily referred to herein for ease of description. In other examples, however, one or both elongated bodies 102, 104 can have another cross-sectional shape, such as an oval or rectangular cross-section. Thus, references to a circumference of elongated bodies 102, 104 or circumferential positions of side holes 108, 114 may also refer generally to positions along an outer perimeter of the respective elongated body 102, 104.

In some examples, as shown in FIG. 1, outer elongated body 104 defines a plurality of outer body side holes 108 that are distributed both longitudinally (along central longitudinal axis L of outer elongated body 104) and circumferentially around outer elongated body 104 (about central longitudinal axis L). For example, as shown in the example of FIG. 1, outer body side holes 108 can be distributed in a helical or spiral pattern around outer elongated body 104, which can include a single helix or spiral or a cross-wound helical or spiral pattern. In some examples, there is only one outer side hole 108 at each particular longitudinal position. In other examples, there are two or more outer body side holes 108 at each particular longitudinal position. The side holes that share a longitudinal position can be spaced, for example, 15 to 180 degrees apart from each other and can be evenly circumferentially spaced apart or unevenly circumferentially spaced from each other. For example, two side holes 108 that are longitudinally aligned can be circumferentially spaced from each other such as 180 degrees apart from each other, i.e., diametrically opposed.

Outer body side holes 108 can have any suitable spacing along longitudinal axis L, which may be referred to as an axial spacing. A distance between two adjacent outer body side holes 108 may be referred to as an axial interval 120. Axial interval 120 may be measured between any two corresponding points of side holes 108, such as the distal most edges, the proximal most edges, the longitudinal center, or the like. Axial interval 120 may have any suitable value, including but not limited to about 15 centimeters (cm) to about 60 cm. "About" may refer to the exact numerical values that or within about 5%-10% of the numerical values or as close to the numerical value as permitted by manufacturing tolerances. In some examples, axial interval 120 may be selected to correspond to desired spacing of targeted fluid delivery within a patient's vasculature.

In some examples, axial interval 120 is the same for all pairs of adjacent side holes 108. In other examples, axial interval 120 may vary for different pairs of side holes. For example, side holes 108 closer to proximal end 104A of elongated body 104 (and, therefore, closer to an entry point into vasculature) may be spaced closer together than more distal side holes 108 to provide a clinician with more options for selectively targeting vessel locations for delivery of a vasodilating agent. For example, axial interval 120 near proximal end 104A can be about 5 cm to about 10 cm, and can increase towards distal end 104B (e.g., moving from a proximal to a distal end of elongated body 104, adjacent side holes 108 may be spaced a 5 cm axial interval, then a 10 cm axial interval, then a 20 cm axial interval, then a 40 cm axial interval, and then a 60 cm interval, although other varying intervals can be used in other examples.

Outer body side holes 108 can span any suitable length of outer elongated body 104, the span being a distance from a proximal-most end of a proximal-most outer side hole 108 to a distal-most end of a distal-most outer side hole 108. For example, in some examples, outer body side holes 108 span about 10 cm to about 80 cm, such as about 60 cm (e.g., 6 holes spaced at 10 cm from an adjacent hole or 4 holes spaced at 15 cm from an adjacent hole). For example, a span of about 10 cm to about 80 cm may be useful in examples in which outer body side holes 108 are used to deliver a vasodilating agent. In other examples, outer body side holes 108 span a larger distance, e.g., a longer length of elongated body 104, e.g., when outer body side holes 108 are used to deliver a contrast agent. More outer body side holes 108 can enable greater granularity of injection distance.

In some examples, outer body side holes 108 are positioned closer to a proximal end 104A of outer elongated body 104 than distal end 104B. This may enable a clinician to deliver a vasodilating agent relatively close to an entry point into vasculature of a patient, such as between 5 and 60 cm from the entry point, where vessel spasms may be more likely to be occurring with some patients and some access sites, such as the radial artery.

Figure 2:
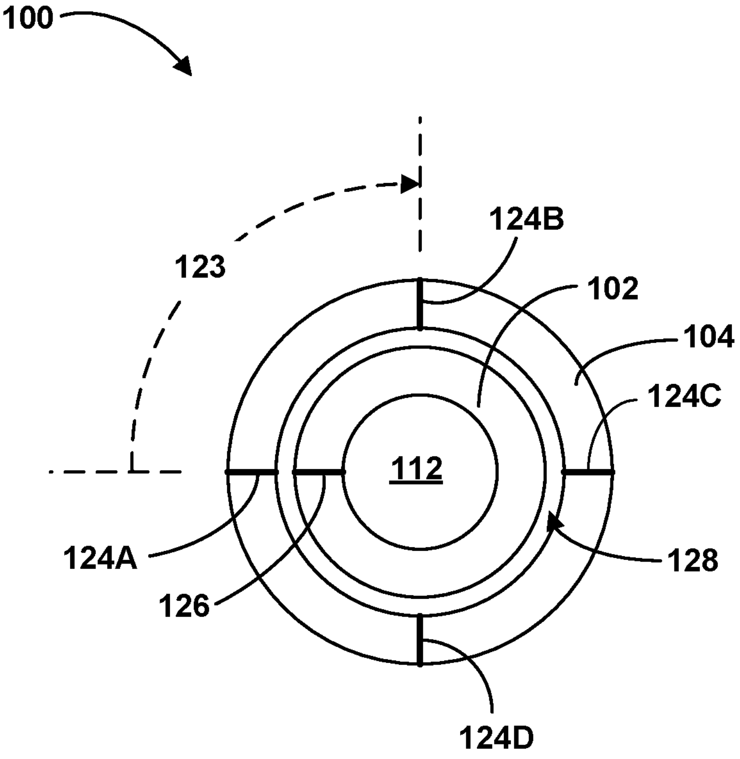
FIG. 2 is a conceptual diagram illustrating an end view of the example introducer assembly of FIG. 1 and illustrates the inner elongated body is received in the outer elongated body.

In examples in which outer body side holes 108 are circumferentially spaced around outer elongated body 104, an outer side hole 108 is spaced from an adjacent outer side hole 108 by a circumferential interval 123 (shown in FIG. 2). The circumferential interval can be any suitable interval, such as, but not limited to, about 15 degrees to about 180 degrees, such as about 30 degrees to about 180 degrees, or about 45 degrees to about 180 degrees, or about 60 degrees to about 180 degrees, or about 90 degrees to about 180 degrees. The circumferential interval may change based on the number of outer body side holes 108 aligned at each longitudinal position and/or the number of longitudinal positions of outer body side holes 108.

In some examples, as shown in FIG. 1, inner elongated body 102 defines a plurality of inner body side holes 114 distributed longitudinally along the inner elongated body 102 (along central longitudinal axis L of inner elongated body 102) and open to the inner body lumen 112. In examples in which outer elongated body 104 defines only one outer side hole 108 at each longitudinal position, inner elongated body 102 is configured to define longitudinally aligned inner body side holes 114 (as opposed to circumferentially distributed inner body side holes). In some examples in which outer elongated body 104 defines multiple outer side hole 108 at each longitudinal position, inner elongated body 102 is configured to define a corresponding number of inner body side holes 114 at each longitudinal position to enable inner body side holes 114 to align with the outer body side holes 108 at a particular longitudinal position.

A longitudinal spacing of inner body side holes 114 (referred to herein as axial interval 122) along longitudinal axis L is based on axial interval 120 of outer body side holes 108 to enable inner and outer body side holes 114, 108 to align (e.g., fully or partially overlap) when inner elongated body 102 is introduced in lumen 106 of outer elongated body 104 and properly clocked (e.g., rotationally oriented with each another). For example, interval 122 can be the about the same (e.g., the same or nearly the same to the extent permitted by manufacturing tolerances) as axial interval 120 of outer body side holes 114, or less than or greater than axial interval 120 but still within a range that enables inner and outer body side holes 114, 108 to align when inner elongated body 102 is introduced in outer body lumen 106. Axial interval 122 may be measured between any two corresponding points of inner body side holes 114, such as the distal most edges, the proximal most edges, the longitudinal center, or the like.

Outer body side holes 108 and inner body side holes 114 may have any suitable shape and size. In some examples, some or all outer body side holes 108 have the same shape and size as some or all inner body side holes 114, such that when an outer side hole 108 is aligned with an inner side hole 114, the outer perimeters of the side holes 108, 114 line up and inner elongated body 102 blocking fluid flow through the respective outer side hole 108. In other examples, however, some or all outer body side holes 108 have a different shape and/or size as some or all inner body side holes 114. Example shapes for side holes 108, 114 include, but are not limited to, circular, oval, square, hexagonal, rectangular, and the like. The size of the side holes 108, 114 can be selected to enable the appropriate volume and flow rate of fluid out of outer body side holes 108. In some examples, each side hole 108, 114 has a diameter of less than or equal to 1 millimeter. In some examples, the size of each side hole is selected to be small enough to reduce the possibility of a guidewire inadvertently extending through the side hole, but large enough to enable a sufficient fluid flow to achieve a desired outcome (e.g., reduction in vessel spasms, visibility via contrast agent, or the like).

For ease of description, an example in which inner elongated body 102 defines a single column of longitudinally aligned inner body side holes 114 and in which outer elongated body 104 defines a helical distribution of outer body side holes 108. In other examples, however, inner elongated body 102 and outer elongated body 104 can define another suitable arrangement of side holes that enable one or more inner body side holes 114 to align with a subset of outer body side holes 108, while inner elongated body 102 blocks passage of fluid through outer body side holes 108. Although four inner body side holes 114 and four outer body side holes 108 are shown in FIG. 1, in other examples, inner and outer elongated bodies 102, 104 can define any suitable number of side holes, such as two, three, five, six, or more than six.

A particular subset of outer body side holes 108 can be used for fluid delivery when the subset of outer body side holes 108 is aligned with one or more inner body side holes 114. The aligned inner and outer body side holes 114, 108 define a fluid pathway from inner body lumen 112 to an environment external to outer elongated body 104. Due to the outer cross-sectional dimension (e.g., outer diameter) of inner elongated body 102 relative to the inner cross-sectional dimension (e.g., inner diameter) of outer elongated body 104, when inner elongated body 102 is positioned in lumen 106 of outer elongated body 104, inner elongated body 102 blocks fluid flow through the outer body side holes 108 that are not aligned with one or more inner body side holes 114. For example, a seal may be created between outer surface 116 of inner elongated body 102 and outer body lumen 106 of outer elongated body 104. In some examples in which fluid is injected through inner body lumen 112 of inner elongated body 102, the seal prevents fluid escape outside any outer body side holes 108 except for those side holes 108 that are aligned with one or more inner body side holes 114. In some examples, fluid may also dispense from the distal open end of the inner elongated body 102. However, in some examples where the distal end of the inner elongated body 102 is closed, fluid is dispersed only through the aligned side holes 108, 114.

A user may, therefore, select different subsets of outer body side holes 108 for fluid delivery by changing the relative rotational orientation of elongated bodies 102, 104 to align different subsets of outer body side holes 108 with one or more inner body side holes 14. In the example shown in FIG. 1, for example, different relative rotational orientations of elongated bodies 102, 104 enable selective fluid delivery at a particular locations along longitudinal axis L.

When inner elongated body 102 is positioned in outer body lumen 106, inner elongated body 102 is configured to rotate relative to outer elongated body 104 between different rotational orientations positions. In some examples, in a first rotational orientation, a first subset of outer body side holes 108 aligns with a first subset of inner body side holes 114 and inner elongated body 102 blocks a second subset of outer body side holes 108, and in a second rotational orientation, the second subset of outer body side holes 108 aligns with a second subset of inner body side holes 114 and inner elongated body 102 blocks the first subset of outer body side holes 108 from lumen 112. There may be a further number of rotational orientations positions which operate in a similar fashion to the first and second rotational orientations. In some examples, there may be a relative rotational orientation of elongated bodies 102, 104 in which no outer body side holes 108 are aligned with inner body side holes 108 from the inner elongated body 102 and in which inner elongated body 102 blocks all outer body side holes 108 from lumen 112.

To facilitate alignment between one or more inner body side holes 114 and different subsets of outer body side holes 108, inner and outer elongated bodies 102, 104 include visible markings 126, 124A-124D (collectively referred to as "markings 124"). Visible markings 126, 124 are at fixed locations on the respective elongated bodies 102, 104, and are located where a user may easily identify the markings 126, 124 and see the markings 126, 124 during a medical procedure.

The relative position of alignment marking 126 relative to the position markings 126 of outer elongated body 104 correspond to different relative rotational orientations of inner elongated body 102 and outer elongated body 104. Thus, the different position markings 124 may correspond to different "clocked" positions of inner elongated body 102 relative to outer elongated body 104. The relative position of the alignment marking 126 and the position markings 124 may indicate which subset of outer body side holes 108 are aligned with a subset of inner body side holes 114 and not blocked by inner elongated body 102.

In order to select different subsets of outer body side holes 108 for fluid delivery, a user may rotate elongated bodies 102, 104 relative to each other (e.g., by rotating one elongated body 102 or 104 while the other elongated body stays rotationally in place, or by rotating both elongated bodies 102, 104) to align marking 126 on inner elongated body 102 with a marking 124A-124D on outer elongated body 104. In the example shown in FIG. 1, each subset of outer body side holes 108 includes one side hole at a respective longitudinal and circumferential position, such that each marking 124 indicates a circumferential position of a respective side hole. As discussed above, however, in other examples, a subset of outer body side holes 108 can include multiple side holes at a respective longitudinal and/or circumferential position. Markings 126, 124A-124D can have any suitable visible indicia, such as a color, text, graphic, texture, or the like, or any combination thereof.

Marking 126 of inner elongated body 102 indicates the circumferential position of inner body side holes 114. Each marking 124A-124D of outer elongated body 104 indicates the circumferential position of a respective outer body side holes 108, and, in some examples, also indicates the longitudinal position of the respective outer body side holes 108. For example, in the example shown in FIG. 1, marking 124A circumferentially aligns with outer side hole 108A, marking 124B circumferentially aligns with outer side hole 108B, marking 124C circumferentially aligns with outer side hole 108C, and marking 124D circumferentially aligns with outer side hole 108D. Markings 124 can also indicate, for example, the relative longitudinal position of the respective outer side hole 108 via textual, graphical, or other visible indicia. In the example shown in FIG. 1, marking 124A includes a corresponding distance value (15 cm), which indicates the longitudinal location of the respective side hole 108. The distance can be, for example, a distance from proximal end 104A of outer elongated body 104 or from another reference point. In other examples, the distance value can be located on another surface of introducer assembly 100, such as on a surface of outer elongated body 104 at proximal end 104A (e.g., the view shown in FIG. 2). Although not shown in FIG. 1, markings 124B-124D can also include corresponding numerical values, such as 30 cm, 45 cm, and 60 cm, respectively.

Other suitable alphanumeric, graphical, or color indications can be used to indicate the longitudinal location of outer body side holes 108 corresponding to each marking 124.

FIG. 2 is an end view of introducer assembly 100 and illustrates inner elongated body 102 introduced in outer body lumen 106 of outer elongated body 104. FIG. 2 illustrates how alignment marking 126 on inner elongated body 102 and a plurality of position markings 124 on the outer elongated body 104 may inform a user of the relative position of side holes on the respective elongated bodies. In some examples, outer body side holes 108 and position markings 124 of the outer elongated body 104 are spaced at the same circumferential interval 123. The circumferential interval 123 may vary based on a total number of outer body side holes 108 having different axial position along the outer elongated body 104.

Figure 4:
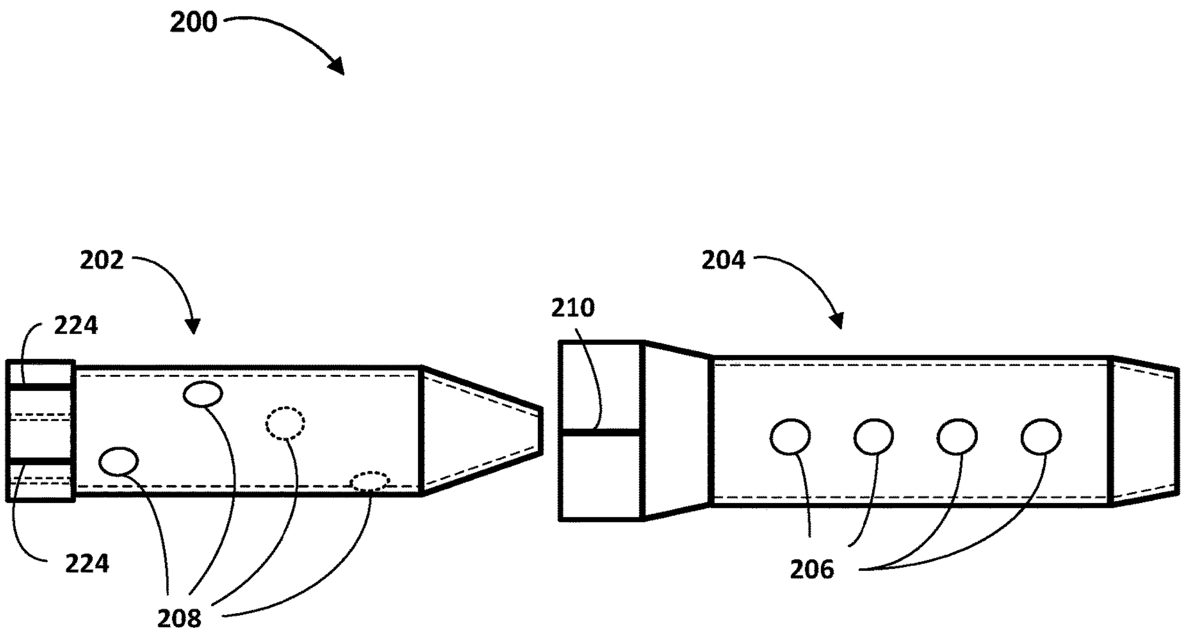
FIG. 4 is a conceptual diagram illustrating another example introducer sheath.

Rotation of the inner elongated body 102 relative to outer elongated body 104 (or vice versa or rotation of both bodies 102, 104) changes which subset of outer sides holes 108 aligns with one or more inner body side holes 114. The aligned subset of outer body side holes 108 and inner body side holes 114 determines the axial position of fluid dispersion from introducer assembly 100. For example, in the example of FIGS. 1 and 2, when inner elongated body 102 is in a first rotational orientation in which alignment marking 126 is aligned with a first position marking 124A of outer elongated body 104, outer side hole 108A is aligned with inner side hole 114A, such that fluid may flow from inner body lumen 112 through inner side hole 114A, and through outer side hole 108A and such that inner elongated body 102 blocks fluid flow through the other outer body side holes 108B-108D. The outer diameter of second elongated body 102 is large enough to create a seal with the inner diameter of outer elongated body 104 to substantially block fluid flow through outer body side holes 108B-108D (e.g., block or reduce fluid flow to a negligible level). While FIG. 4 is shown with a radial gap 128 between inner elongated body 102 and outer elongated body 104, gap 128 may be substantially negligible, or there may even be an interference fit between inner elongated body 102 and outer elongated body 104.

When inner elongated body 102 is in a second rotational orientation in which alignment marking 126 is aligned with position marking 124B, outer side hole 108B is aligned with inner side hole 114B, such that fluid may flow from inner body lumen 112 through inner side hole 114B, and through outer side hole 108B and such that inner elongated body 102 blocks fluid flow through the other side holes 108A, 108C, and 108D. Inner elongated body 102 can also be placed in a third rotational orientation in which alignment marking 126 is aligned with position marking 124C and a fourth rotational orientation in which alignment marking 126 is aligned with position marking 124D to provide similar fluid pathways through the respective side holes 108C, 108D.

In some examples, to move inner elongated body 102 from one (relative) rotational orientations to another, a user may rotate inner elongated body 102 (or outer elongated body 104) by a circumferential interval 123. The user may use alignment marking 126 of inner elongated body 102 and position markings 124 of outer elongated body 104 to determine the different rotational orientations and, therefore, the different fluid pathways for fluid to flow out of outer body side holes 108.

While the example in FIGS. 1 and 2 shows four position markings 124 on outer elongated body 104 at a regular circumferential interval 123, the number of position markings (and number of outer body side holes) can vary in different examples. Additionally, the circumferential interval 123 between adjacent position markings 124 need not be regular. In some examples, the position markings 448 on the outer elongated body 440 may be a line, but can also be any other suitable shape, such as a dot, square, or even text describing the axial position of the corresponding side hole.

FIG. 3 is a conceptual diagram illustrating a side view of introducer assembly 100, in which inner elongated body 102 is introduced in lumen 106 of outer elongated body 104. In FIG. 3, inner elongated body 102 is in a first rotational orientation relative to outer elongated body 104, such that outer side hole 108A is aligned with inner side hole 114A, which enables fluid to flow from inner body lumen 112, through side holes 114A, 108A, and to an environment external to outer elongated body 104. Side holes 108A, 114A are partially aligned in FIG. 3, but can be fully aligned in other examples to maximize the area through which fluid can flow out of inner body lumen 112 to an environment external to outer elongated body 104. As FIG. 4 illustrates, in the first rotational orientation, inner elongated body 102 covers the other outer body side holes 108B-108D and blocks fluid flow out of lumen 112 through the other outer body side holes 108B-108D.

In some examples, introducer assembly 100 includes a fluid port assembly 130 connected to a proximal portion of inner elongated body 102, which is fluidically connected inner body lumen 112 and can be used to deliver a fluid to inner body lumen 112. Fluid introduced into inner body lumen 112 through fluid port assembly 130 exits introducer assembly 100 at a location where a subset of outer body side holes 108 aligns with a subset of inner body side holes 114. In some examples, inner elongated body 102 can include a hemostatic sealing valve or another suitable valve, the valve being configured to help prevent fluid flow through proximal end 102*a*. The valve can be, for example, positioned at proximal end 102A or at another location. This may enable fluid to be introduced into fluid port assembly 130 with or without a guidewire in lumen 112 of inner elongated body 102 and not leak out proximal end 102*a*.

As discussed above, inner body side holes 114 and outer body side holes 108 can be distributed along the respective elongated bodies in different ways in different examples. FIG. 4 is a conceptual diagram illustrating a side view of another example introducer assembly 200, which include an inner elongated body 202 and an outer elongated body 204, which are similar to inner elongated body 102 and an outer elongated body 104, respectively, except for the arrangement of side holes. In particular, outer body side holes 206 of outer elongated body 204 are circumferentially aligned with each other, similar to the arrangement of inner body side holes 114 of inner elongated body 102 of FIGS. 1-3, and inner body side holes 208 of inner elongated body 202 are longitudinally and circumferentially distributed relative to each other (e.g., helically arranged), similar to the arrangement of outer body side holes 108 of outer elongated body 104 of FIGS. 1-3.

Different subsets of outer body side holes 206 can be selected for fluid delivery by modifying a relative rotational orientation of inner and outer elongated bodies 202, 204, e.g., in a manner similar to that described above with respect to introducer assembly 100. Alignment marking 210 indicates the circumferential position of outer body side holes 206 and position markings 224 indicates the circumferential and longitudinal position of inner side holes 208, e.g., as described with respect to markings 224 in FIGS. 1-3.

Figure 5:
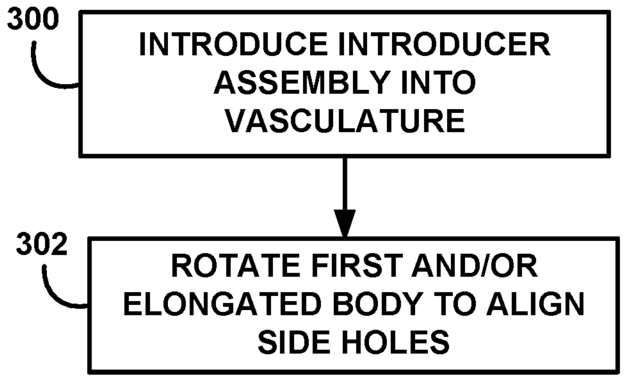
FIG. 5 is a flow diagram illustrating an example method for using an introducer sheath.

FIG. 5 is a flow diagram illustrating an example technique of using an introducer assembly described herein to selectively deliver fluid through a subset of side holes of an introducer assembly to a target location in vasculature of a patient. While FIG. 5 is described with reference to introducer assembly 100 of FIGS. 1-3, in other examples, the technique of FIG. 5 may be used with other introducer assemblies described herein, including introducer assembly 200 of FIG. 4.

In accordance with the technique shown in FIG. 5, a user introduces introducer assembly 100 into vasculature of a patient (300), e.g., with the aid of a guidewire or other device. This can be done as part of any suitable medical procedure, such as, but not limited to, a percutaneous coronary intervention (PCI) procedure. The user selects subset of outer body side holes 108 for delivering a fluid into the vasculature and rotates first and second elongated bodies 102, 104 relative to each other to align the subset of outer body side holes 108 with one or more inner body side holes 114 (302). For example, the user can rotate one elongated body 102 or 104, or rotate both elongated bodies 102, 104 to move inner elongated body 102 to a first rotational orientation in which the subset of outer body side holes 108 (e.g., side hole 108A) is aligned with one or more inner body side holes 114 (e.g., inner side hole 114). The user can thereafter introduce a fluid into inner body lumen 112 via fluid port 130, which flows through lumen 112 and exits lumen 112 through the first subset of outer body side holes 108, through the one or more inner side hole 114 aligned with the first subset of outer body side holes 108, and to an environment external to outer elongated body 104.

The user may use markings 124, 126 to identify the desired relative rotational orientation of the elongated bodies 102, 104. For example, in examples in which the subset of outer body side holes 108 is outer side hole 108A, the user can rotate one or both elongated bodies 102, 104 until alignment marking 126 on inner elongated body 102 is aligned with (e.g., lined up in a direction parallel to longitudinal axis L) position marking 124A, which indicates the circumferential position of outer side hole 108A on elongated body 104. When markings 124A, 126 are aligned, outer side hole 108A uncovered by inner elongated body 102 and the other outer body side holes 108B-108D are blocked by inner elongated body 102. This enables fluid to flow through inner body lumen 112, through inner side hole 114A, and through outer side hole 108A to exit introducer assembly 100.

In some examples, the clinician selects subset of outer body side holes 108 for fluid delivery by at least determining a target location in the blood vessel and selecting the subset of outer body side holes 108 having a relatively close axial position along central longitudinal axis L and/or a circumferential position about central longitudinal axis L to the target location. In other examples, the clinician may select the subsets of outer body side holes 108 in a particular order, e.g., starting with a proximal-most, distal-most, or middle subset, until the desired outcome (e.g., dilation of the blood vessel) is achieved.

In some examples, the technique of FIG. 5 may further include rotating inner elongated body 102 within lumen 106 of outer elongated body 104 to one or more different rotational orientations to select different subset of outer body side holes 108 for fluid delivery and subsequently introduce a fluid into inner body lumen 112 via fluid port 130 to deliver the fluid through the different subsets of outer body side holes 108.

The technique of FIG. 5 may include further steps, such as withdrawing inner elongated body 102 from lumen 106 of outer elongated body 104, inserting a medical device through inner body lumen 112 or outer body lumen 106, or any combination thereof.

Various examples have been described. Any combination of the described systems, devices, operations, or functions is contemplated. These and other examples are within the scope of the following claims.

What is claimed is:

1. A medical assembly comprising:

an outer elongated body defining an outer body lumen and a plurality of outer body side holes distributed longitudinally along the outer elongated body and open to the outer body lumen; and an inner elongated body defining an inner body lumen and a plurality of inner body side holes distributed longitudinally along the inner elongated body and open to the inner body lumen, the inner elongated body being configured to be inserted in the outer body lumen, wherein when the inner elongated body is positioned in the outer body lumen, the inner elongated body is configured to rotate relative to the outer elongated body between:

a first rotational orientation in which a first subset of outer body side holes aligns with a first subset of inner body side holes and in which the inner elongated body blocks a second subset of outer body side holes, and a second rotational orientation in which the second subset of outer body side holes aligns with a second subset of inner body side holes and in which the inner elongated body blocks the first subset of outer body side holes, and wherein the outer elongated body is an introducer sheath and the inner elongated body is a dilator.

2. The medical assembly of claim 1, wherein the plurality of outer body side holes are longitudinally spaced at an axial interval along the outer elongated body and wherein the plurality of inner body side holes are longitudinally spaced at the axial interval along the inner elongated body.

3. The medical assembly of claim 2, wherein the axial interval is 15 centimeters to about 60 centimeters.

4. The medical assembly of claim 1, wherein the plurality of outer body side holes are evenly spaced along a longitudinal axis of the outer elongated body.

5. The medical assembly of claim 1, wherein the plurality of outer body side holes are unevenly spaced along a longitudinal axis of the outer elongated body.

6. The medical assembly of claim 1, wherein the plurality of outer body side holes are circumferentially spaced around the outer elongated body and the plurality of inner body side holes are longitudinally aligned along the inner elongated body.

7. The medical assembly of claim 6, wherein the outer elongated body comprises:

a first marking configured to indicate a first circumferential position of the first subset of outer body side holes along a circumference of the outer elongated body; and a second marking configured to indicate a second circumferential position of the second subset of outer body side holes along the circumference of the outer elongated body, and wherein the inner elongated body comprises a third marking configured to indicate a third circumferential position of the plurality of inner body side holes along a circumference of the inner elongated body.

8. The medical assembly of claim 1, wherein the plurality of outer body side holes are longitudinally aligned along the outer elongated body and the plurality of inner body side holes are circumferentially spaced around the inner elongated body.

9. The medical assembly of claim 8, wherein the inner elongated body comprises:

a first marking configured to indicate a first circumferential position of the first subset of inner body side holes along a circumference of the inner elongated body; and a second marking configured to indicate a second circumferential position of the second subset of inner body side holes along the circumference of the inner elongated body, and wherein the outer elongated body comprises a third marking configured to indicate a third circumferential position of the plurality of outer body side holes along a circumference of the outer elongated body.

10. The medical assembly of claim 1, wherein a diameter of the plurality of outer body side holes is less than or equal to 10 millimeters.

11. The medical assembly of claim 1, wherein the inner elongated body defines a closed distal end.

12. An introducer assembly comprising:

an introducer sheath defining an introducer sheath lumen and a plurality of introducer sheath side holes distributed longitudinally along the introducer sheath and open to the introducer sheath lumen; and an inner member defining an inner member lumen and a plurality of inner member side holes distributed longitudinally along the inner member and open to the inner member lumen, wherein when the inner member is inserted in the introducer sheath lumen, different subsets of introducer sheath side holes are configured to align with one more of the inner member side holes depending on a rotational orientation of the introducer sheath and the inner member to enable selective fluid delivery through a subset of introducer sheath side holes from the inner member lumen, and wherein the inner member is a dilator.

13. The introducer assembly of claim 12, wherein the introducer sheath is more flexible than the inner member.

14. The introducer assembly of claim 12, wherein the plurality of introducer sheath side holes are circumferentially spaced around the introducer sheath and the plurality of inner member side holes are longitudinally aligned along the inner member.

15. The introducer assembly of claim 12, wherein the plurality of introducer sheath side holes are longitudinally aligned along the introducer sheath and the plurality of inner member side holes are circumferentially spaced around the inner member.

16. A method comprising:

introducing a medical assembly into vasculature of a patient, the medical assembly comprising:

an outer elongated body defining an outer body lumen and a plurality of outer body side holes distributed longitudinally along the outer elongated body and open to the outer body lumen; and an inner elongated body defining an inner body lumen and a plurality of inner body side holes distributed longitudinally along the inner elongated body and open to the inner body lumen, the inner elongated body being configured to be inserted in the outer body lumen, wherein when the inner elongated body is positioned in the outer body lumen, the inner elongated body is configured to rotate relative to the outer elongated body between:

a first rotational orientation in which a first subset of outer body side holes aligns with a first subset of inner side and in which the inner elongated body blocks a second subset of outer body side holes, and a second rotational orientation in which the second subset of outer body side holes aligns with a second subset of inner body side holes and in which the inner elongated body blocks the first subset of outer body side holes, and wherein the outer elongated body is an introducer sheath and the inner elongated body is a dilator; and rotating at least one of the inner elongated body or the outer elongated body to position the inner elongated body in the first rotational orientation.

17. The method of claim 16, further comprising:

after the inner elongated body in the first rotational orientation, introducing a fluid through the inner body lumen, wherein the fluid exits the outer elongated body and the inner elongated body where the first subset of outer body side holes aligns with a first subset of inner body side holes.

18. The method of claim 16, further comprising:

rotating at least one of the inner elongated body or the outer elongated body to position the inner elongated body in the second rotational orientation; and after the inner elongated body in the second rotational orientation, introducing a fluid through the inner body lumen, wherein the fluid exits the outer elongated body and the inner elongated body where the second subset of outer body side holes aligns with the second subset of inner body side holes.

19. A medical assembly comprising:

an outer elongated body defining an outer body lumen and a plurality of outer body side holes distributed longitudinally along the outer elongated body and open to the outer body lumen; and an inner elongated body defining an inner body lumen and a plurality of inner body side holes distributed longitudinally along the inner elongated body and open to the inner body lumen, the inner elongated body being configured to be inserted in the outer body lumen, wherein when the inner elongated body is positioned in the outer body lumen, the inner elongated body is configured to rotate relative to the outer elongated body between:

a first rotational orientation in which a first subset of outer body side holes aligns with a first subset of inner body side holes and in which the inner elongated body blocks a second subset of outer body side holes, and a second rotational orientation in which the second subset of outer body side holes aligns with a second subset of inner body side holes and in which the inner elongated body blocks the first subset of outer body side holes, and wherein the inner elongated body defines a closed distal end.

* * * * *